US009879311B2

(12) United States Patent
Gosiewski et al.

(10) Patent No.: US 9,879,311 B2
(45) Date of Patent: Jan. 30, 2018

(54) METHOD FOR EFFICIENT ISOLATION OF MICROBIAL DNA FROM BLOOD

(71) Applicant: UNIWERSYTET JAGIELLOŃSKI, Kraków (PL)

(72) Inventors: Tomasz Gosiewski, Kraków (PL); Monika Brzychczy-Włoch, Kraków (PL)

(73) Assignee: UNIWERSYTET JAGIELLONSKI, Krakow (PL)

( * ) Notice: Subject to any disclaimer, the term of this patent is extended or adjusted under 35 U.S.C. 154(b) by 260 days.

(21) Appl. No.: 14/422,860

(22) PCT Filed: Aug. 23, 2013

(86) PCT No.: PCT/PL2013/000109
§ 371 (c)(1),
(2) Date: Feb. 20, 2015

(87) PCT Pub. No.: WO2014/031018
PCT Pub. Date: Feb. 27, 2014

(65) Prior Publication Data
US 2015/0240290 A1    Aug. 27, 2015

(30) Foreign Application Priority Data
Aug. 24, 2012   (PL) .......................................... 400501

(51) Int. Cl.
*C12Q 1/68*      (2006.01)
*C12N 15/10*    (2006.01)

(52) U.S. Cl.
CPC ....... *C12Q 1/6806* (2013.01); *C12N 15/1003* (2013.01)

(58) Field of Classification Search
None
See application file for complete search history.

(56) References Cited

U.S. PATENT DOCUMENTS

| 6,605,439 B2 | 8/2003 | Einsele et al. |
| 7,670,768 B1 | 3/2010 | Heath et al. |
| 2011/0300608 A1 | 12/2011 | Ryan et al. |

FOREIGN PATENT DOCUMENTS

| WO | 9707238 A3 | 7/1997 |
| WO | 02055737 A1 | 7/2002 |
| WO | 2009015484 A1 | 2/2009 |
| WO | 2012050787 A1 | 4/2012 |

OTHER PUBLICATIONS

International Search Report for App. No. PCT/PL2013/000109 filed Nov. 20, 2013.
Urszula Nawrot et al: "Comparison of the utility of five commercial kits for extraction of DNA from Aspergillus fumigatus spores Introduction", Oct. 27, 2010 (Oct. 27, 2010).
De Boer R et al: "Improved detection of microbial DNA after bead-beating before DNA isolation", Journal of Microbiological Methods, Elsevier, Amsterdam, NL, vol. 1. 80, No. 2, Feb. 1, 2010 (Feb. 1, 2010), pp. 209-211, XP026872053, ISSN: 0167-7012.
Hogg G M et al: "Rapid detection of methicillin-susceptible and methicillin-resistant *Staphylococcusaureus* directly from positive BacT/Alert<(>R) blood culture bottles using real-time polymerase chain reaction: evaluation and comparison of 4 DNA extraction methods", Diagnostic Microbiology and Infectious Diseases, Elsevier Science Publishing Co., Amsterdam, NL, vol. 61, No. 4, Aug. 1, 2008 (Aug. 1, 2008) pp. 446-452, XP022931494, ISSN: 0732-8893.
L. Metwally et al: "Improving molecular detection of Candida DNA in whole blood: comparison of seven fungal DNA extraction protocols using real-time PCR", Journal of Medical Microbiology, vol. 57, No. 3, Mar. 1, 2008 (Mar. 1, 2008), pp. 296-303, XP055089108, ISSN: 0022-2615.

*Primary Examiner* — David C Thomas
(74) *Attorney, Agent, or Firm* — Renner Kenner Greive Bobak Taylor & Weber

(57) ABSTRACT

A method allows the simultaneous isolation of bacterial and fungal DNA from blood. The method uses the enzymatic, mechanical and thermal lysis.

5 Claims, 5 Drawing Sheets

METHOD FOR EFFICIENT ISOLATION OF MICROBIAL DNA FROM BLOOD

TECHNICAL FIELD

The application relates to methods for isolating microbial DNA from blood samples to obtain a high-quality material for molecular diagnostic PCR.

BACKGROUND

Microbiological diagnosis of blood is one of the most problematic diagnostic challenges. The presence of bacteria (bacteremia) or fungi (fungemia) in the blood very often results in sepsis-systemic inflammation caused by the infection.

Sepsis is one of the most pressing problems of modern medicine. Mortality caused by sepsis of bacterial or fungal etiology is very high in Poland [Martin G. S., Mannino D. M., i Moss M., *The epidemiology of sepsis in the United States from 1979 through 2000*. N Engl J Med, 2003. 348: str. 1546-1554; Zielinski A. i Czarkowski M. P., *Choroby zakaźne w Polsce w 2005 roku*. Przegl Epidemiol, 2007, 61: str. 177-187].

Lever et al reported that more than 750,000 people die each year due to sepsis in United States [Lever A. and M. I., *Sepsis: definition, epidemiology and diagnosis*. Clinic Rev, 2008. 335(27):879-883]. In the European Union there are more than 146000 fatal cases each year due to severe sepsis. In the UK alone the mortality ranges from 30 to 50/100000 per year, which places sepsis on the top ten leading causes of death [Zielinski A. and Czarkowski M. P., 2007]. Moreover, even in the developed countries sepsis occurs in 2-4 newborns per 1000 and it is the main cause of newborn death [Baltimore R. S., *Neonatal sepsis: epidemiology and management*. Pediatr Drugs, 2003. 5(11):723-740; Watson R. S. and Carcillo J. A., *Scope and epidemiology of pediatric sepsis*. Pediatr Crit Care Med, 2005. 6(3):3-5]. In Poland, there is no accurate epidemiological data, but Zielinski et al indicate that in 2005 there were 967 deaths (including 43 deaths in childhood) due to sepsis.

The most important and most difficult problem in the treatment of bloodstream infections, determining the effectiveness of therapy and, consequently, the cost and time of hospitalization, is the effective diagnosis of factors responsible for the systemic inflammatory response in the course of sepsis. Determination of etiologic factors allows for selection of the most appropriate antibiotic therapy. The material subjected to diagnostic testing is the blood taken from the patient showing clinical signs of sepsis. Currently, the "gold standard" diagnostic method is testing for microbial growth after inoculation in culture media specific to selected pathogen's groups. This method is relatively simple and inexpensive, but also time-consuming—results can take as long as 5 days to become available. Moreover, the identification of pathogens with this method is often unsuccessful due to low sensitivity; microbial growth can be detected only at about 15-20% of the cultures [Jamal W. et al., *Comparative evaluation of BacT/ALERT 3D and BACTEC systems for the recovery of pathogens causing bloodstream infections*. Med Princ Pract, 2006. 15(3):223-227].

Detection of microbiological agents in the blood can be improved using molecular detection methods based on polymerase chain reaction. The sensitivity of molecular methods is much higher than with the culture methods. Moreover, early application of antibiotic therapy does not affect the results of the test due to the fact that there is no need for the growth of bacteria or fungi on the culture medium, but only a detection of the DNA or RNA sequence [Klouche M. and Schroder U., *Rapid methods for diagnosis of bloodstream infections*. Clin Chem Lab Med, 2008. 46(7):888-908].

The classical method of isolating DNA from cells is that the starting material is taken up in denaturing and reducing conditions, often using at the same time enzymes that degrade proteins, and the nucleic acid fractions are then purified by phenol-chloroform extraction, and it is separated from the aqueous phase using dialysis or alcohol precipitation [Sambrock J., Fritsch E. F., Manitias T, 1989, CSH, "Molecular Cloning"]. This method, however, is labor-intensive and time-consuming, and it requires the use of organic solvents, particularly the toxic phenol.

The method proposed in U.S. Patent No. 2011300608 provides total DNA isolation without use of toxic solvents. According to this method a blood sample is suspended in a mixture of anticoagulant and a fixing agent, and a sample is mixed with the erythrocyte lysis buffer. In the next step, the sample is mixed with nuclear lysis buffer, and then with proteinase K and alcohol. The erythrocyte lysis buffer includes the ammonium chloride, ammonium bicarbonate, and a chelating agent such as EDTA.

Also in the patent application WO02055737 there is a method, which avoids the use of toxic solvents, and chaotropic salts. According to this method there is carried out red blood cells lysis, and the white blood cells are removed from the mixture, washed out and then lysed. After that a protein is precipitated from the mixture. All the above mentioned steps are carried out using aqueous solutions. The erythrocyte lysis buffer consists of the ammonium chloride, sodium bicarbonate and EDTA. The leukocyte lysis solution contains a surface-active agent such as sodium lauryl sulfate. The solution used for the precipitation of protein contains an organic salt such as the ammonium acetate.

The above-described methods are used for the eukaryotic DNA isolation e.g. from leukocytes, but these methods are not effective in the case of fungi due to the different chemical composition of their cell wall. A similar method of DNA isolation from fungi has been described in U.S. patent application US2002115077. This method is carried out in the following steps: disintegration of blood cells, isolation of the intact fungal cells, disintegration of the isolated fungal cells and fungal DNA isolation. A preliminary disintegration of erythrocytes is carried out by the osmotic hemolysis and the disintegration of leukocytes—by the enzymatic digestion. Disintegration of fungal cells is carried out by treatment with alkaline lysis and the enzyme. Fungal DNA isolation is carried out by precipitating the protein using potassium acetate and then precipitating the DNA from the supernatant with cold isopropanol. DNA obtained by this method is suitable for amplification using the PCR method.

Unfortunately, the methods of molecular biology also have limitations in conducting microbiological diagnostic of blood. A difficulty is to isolate DNA template of adequate quality and high concentration. The cells of bacteria and fungi show different susceptibility to lysis, which is a prerequisite for obtaining DNA from them. Bacteria are divided into Gram-negative bacteria and Gram-positive bacteria—it is related to the construction of the cell wall. In the case of bacteria, the cell wall of the species from Gram-positive group is thicker and resistant to degradation, which makes it necessary to use special enzymatic lysis (lysozyme, mutanolysin and/or lysostaphin). The fungal cell wall, on the other hand, has completely different chemical composition than the bacterial wall, so standard procedures used with bacteria fail. In addition, the cell walls of yeast-like fungi and mold fungi are structurally different, which greatly complicates the process of DNA isolation.

Molecular diagnostics is also impaired by the heme present in the blood, which is a potent inhibitor of DNA polymerases used in the PCR methods [Abu Al-Soud P. and Randstrom P., *Purification and Characterization of PCR-Inhibitory Components in Blood Cells*. J Clinic Microbiol, 2001. 39(2):485-493]. Most of the available blood processing procedures does not allow for the complete elimination of the PCR inhibition effect, which in turn may lead to a false negative diagnostic result [Akane A., Matsubara K., and Nakamura H., *Identification of the heme compound copurified with deoxyribonucleic acid (DNA) from bloodstains a major inhibitor of polymerase chain reaction amplification*. J Forensic Sci, 1994. 37:362-372]. Heme causes a separation of DNA polymerase (a disintegration of enzyme-substrate complex) and it also blocks the catalytic pocket of the enzyme. In the literature there are reports on different types of sample preparation in order to eliminate the effect of PCR inhibition. Typically, these methods involve a highly accurate washing sample or dilution or adding to the mixture e.g. bovine serum albumin (BSA), glycerol or dextran, which are the additional targets for inhibitors and therefore they reduce the effect on DNA polymerase [Kreader C., *Relief of Amplification Inhibition in PCR with Bovine Serum Albumin or T4 Gene 32 Protein*. Appl. Environ. Microbiol, 1996. 62:1102-1106; Rädström P., Abu Al-Soud P., and Lantz P., *A sample preparation method which facilitates detection of bacteria in blood cultures by the polymerase chain reaction*. J Microbiol Methods 1998. 21:217-224; Michael D., et al, *Removal of PCR inhibitors from soil DNA by chemical flocculation*. J Microbiol Methods, 2003. 52: str. 389-393].

Such activities, however, cause a loss of sensitivity of PCR method, and thus result in less effective diagnostic. There is also the possibility to choose a specific polymerase enzyme from a number of thermostable DNA polymerases used in PCR (Taq, Pwo, Pfu, Tfl, et al.) with the different sensitivity to inhibitors [Abu Al-Soud P., and Lantz P., 1998].

In the scientific and patent literature there appears to be no suitable description of a DNA isolation method from blood, which is effective for both bacteria and fungi. Available descriptions refer to the eukaryotic DNA isolation from leukocytes or separately from bacteria or fungi [Chiba N., Murayama S. Y., Morozumi M., Nakayama E, Okada T., Iwata S., Sunakawa K., Ubukata K., *Rapid detection of eight causative pathogens for the diagnosis of bacterial meningitis by real-time PCR*. J Infect Chemother, 2009. 15:92-98; Sugita S., Kamoi K., Ogawa M, Watanabe K., Shimizu N, Mochizuki M., *Detection of Candida and Aspergillus species DNA using broad-range real-time PCR for fungal endophthalmitis*. Graefes Arch Clin Exp Ophthalmol, 2012. 250:391-398; Badiee P. and Alborzi A., *Detection of Aspergillus species in bone marrow transplant patients*. J Infect Dev Ctries 2010. 4:511-516].

The SeptiFastLys product with kit MagNALyser device has been available on the market for a few years. The principle of the operation is probably based on the mechanical degradation of cells followed by the purification of DNA from proteins with a protease. After lysis, the samples are incubated at a raised temperature with a protease and the chaotropic lysis buffer. After the addition of binding buffer the mixture is transferred to a rotating column containing a filter cartridge with glass fiber. The human genomic DNA and bacterial/fungal target DNA collect on the surface of the glass fiber. Unbound substances such as salts, proteins and other contaminants of cellular origin, are removed in two stages of washing. After the washing the adsorbed nucleic acids are eluted at a raised temperature. The eluates are submitted to PCR analysis. The lysis buffer and binding buffer have the same composition and they comprise the guanidine thiocyanate, Tris-HCl (hydrochloride tris (hydroxymethyl) aminomethane), a nonionic surfactant-polymer ether-polyethylene glycol (PEG), and p-octylphenol (Triton X-100). The enzyme is proteinase K.

These prior methods may benefit from improvements.

SUMMARY OF DISCLOSURE

An exemplary method allows the simultaneous isolation of microbial DNA from the blood. In this method the isolation is carried out by compilation of enzymatic, mechanical and thermal lysis. This approach enables DNA to be obtained from all types of organisms, irrespective of the structure of the cells.

DETAILED DESCRIPTION

Figure 1:
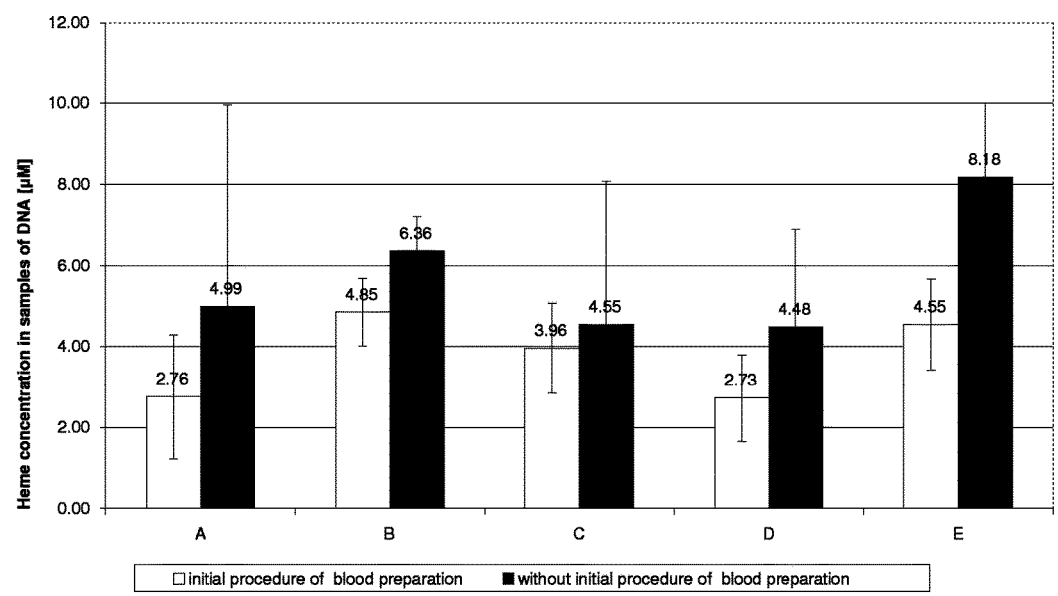
FIG. 1 is a chart that shows the degree of purification of DNA isolate from heme after application of pre-treatment of blood samples according to the exemplary methods and without a pre-treatment.
Figure 2:
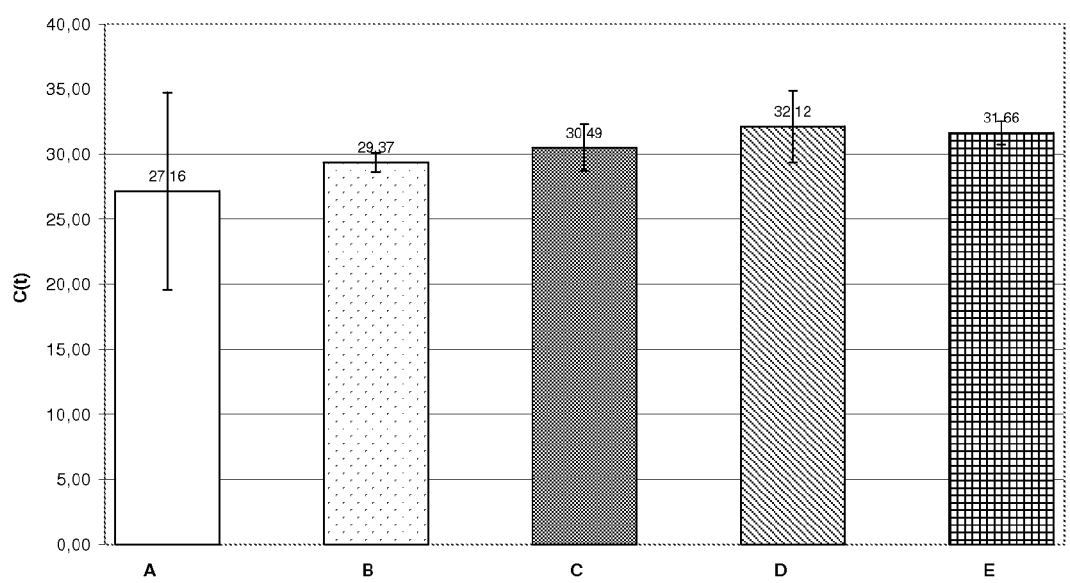
FIG. 2 is a chart that shows the values obtained as a result of the PCR reaction parameter C (t)—the number of the reaction cycle in which a registered linear increase of the amplification product cut the arbitrarily set baseline (at 30 units of fluorescence), for DNA of *Staphylococcus aureus*, using a blood sample pretreatment method according to an exemplary embodiment.
Figure 3:
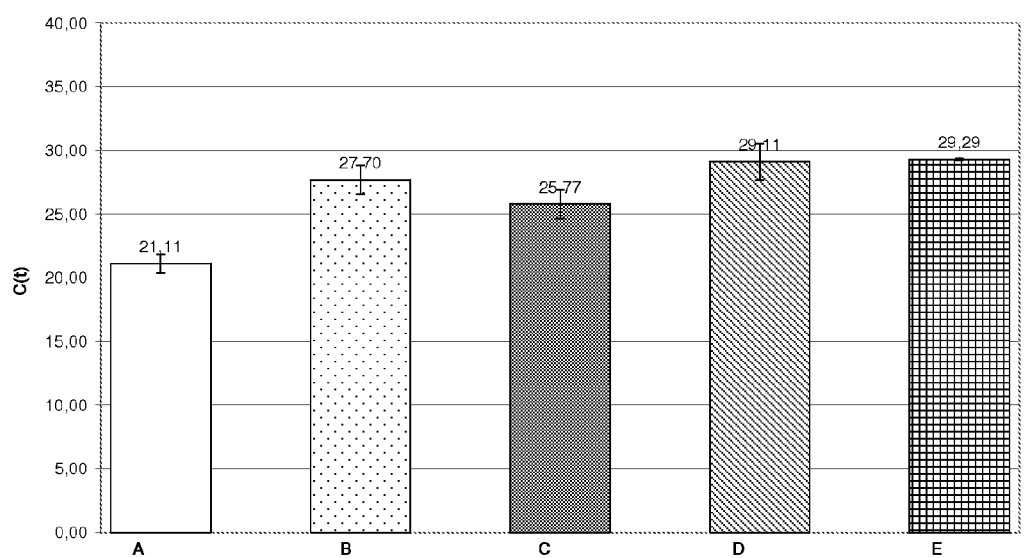
FIG. 3 is a chart that shows the values obtained as a result of the PCR reaction parameter C (t)—the number of the reaction cycle in which a registered linear increase of the amplification product cut the arbitrarily set baseline (at 30 units of fluorescence), for DNA of *Escherichia coli*, using a blood sample pretreatment method according to an exemplary embodiment.
Figure 4:
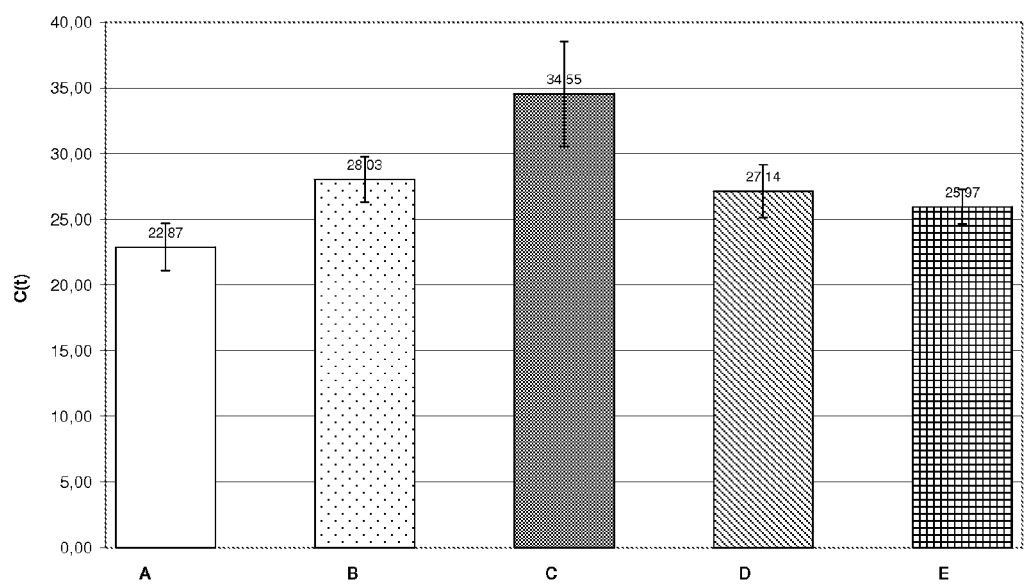
FIG. 4 is a chart that shows the values obtained as a result of the PCR reaction parameter C (t)—the number of the reaction cycle in which a registered linear increase of the amplification product cut the arbitrarily set baseline (at 30 units of fluorescence), for DNA of *Candida albicans*, using a blood sample pretreatment method according to an exemplary embodiment.
Figure 5:
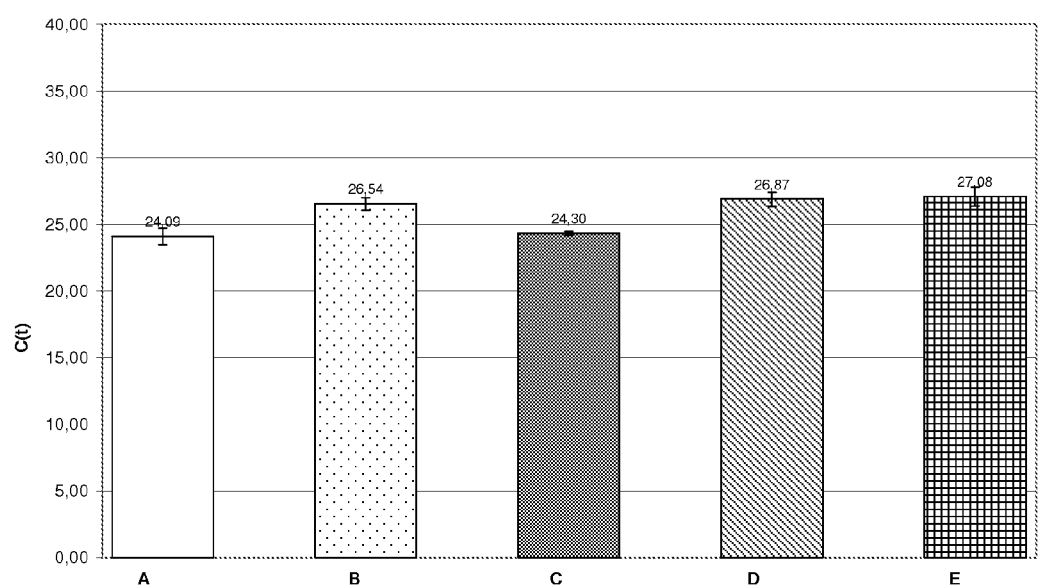
FIG. 5 is a chart that shows the values obtained as a result of the PCR reaction parameter C (t)—the number of the reaction cycle in which a registered linear increase of the amplification product cut the arbitrarily set baseline (at 30 units of fluorescence), for DNA of *Aspergillus* spp, using a blood sample pretreatment method according to an exemplary embodiment.

An exemplary method includes the following steps:

a) an aqueous of ammonium chloride (at a concentration 0.10-0.25 M) is added to the whole blood sample, in a ratio of 1:3 to 1:6 in relation to the volume of the blood sample, the sample is incubated at a temperature of 35° C. to 40° C. from 15 to 30 minutes, followed by centrifugation and removal of supernatant;

b1) optionally the precipitate obtained in step (a) is suspended in a solution of lysozyme at a concentration of 2 to 5 mg/ml, and lysostaphin at a concentration of 0.2 to 0.5 mg/ml in PBS buffer, the suspension is vortexed or shaken and the supernatant is removed;

c) the material obtained in step (a) or (b1) is subjected to mechanical disintegration;

b2) in the case of performing step (b1) the material is incubated at a temperature of 35° C. to 39° C., from 20 to 50 minutes, after that d) a solution of NaOH or KOH (at a concentration of 0.65 to 0.8 mM) is added, in a ratio from 1:1 to 1:3 in relation to the volume of the material of step (c), the material is incubated at a temperature of 80° C. to 95° C., from 5 to 10 minutes, the suspension is centrifuged and the supernatant is removed; followed by adding a buffer (pH of about 7.5) containing Tris-HCL, EDTA, and β-mercaptoethanol, and lyticase with enzymatic activity of 30 to 50 U, the sample is incubated at a temperature of 35° C. to 39° C., from 20 to 50 minutes;

and/or e) the solution is centrifuged and the supernatant is removed.

The mechanical disintegration step (step c) is preferably carried out using glass beads. In a step (d) there is preferably used a buffer consisting of 50 mM Tris-HCl, 10 mM EDTA and 28 mM β-mercaptoethanol. The obtained precipitate is treated in accordance with the manufacturer's instructions for a DNA isolation kit. It is usually a lysis by proteinase K followed by transfer to the columns for DNA, where the pollution is removed.

In the exemplary methods a blood sample pretreatment with ammonium chloride (step a) provides the disruption (hemolysis) of erythrocytes, which causes the release of hemoglobin and its subsequent separation with the supernatant. In the following stages there are present trace amounts of heme, whereas the present remains of erythrocytes in the sample are not an obstacle for effective DNA isolation. After removal of heme, there are introduced the enzymes (lysozyme and lysostaphin) into the sample, which degrade the cell walls of Gram-positive bacteria. Before the incubation of the sample with the enzymes there is carried out a mechanical lysis, to give an additional disruption of cell walls, both bacterial and fungi. In a step (d) an addition of NaOH or KOH "relaxes" the cell walls of fungi at a high temperature, a lyticase digests the cell walls of fungi and β-mercaptoethanol degrades the proteins and helps in the operation of lyticase digestion of fungal walls. The precipitate containing the digested microbial cells and leukocytes is separated out in step (e). The obtained precipitate is a mixture of nucleic acids and proteins. This product can be treated with a DNA isolation kit, which consists of digestion and removal of proteins, and the determination of nucleic acids.

The exemplary method can be used in full mode, in which both bacterial and fungal DNA is isolated, or in limited modes that allow for obtaining DNA only from bacteria or only from fungi.

As a result of the exemplary methodology of blood preparation there is obtained a material from which can be isolated the highly purified DNA of all microorganisms using the commercial DNA isolation kits. The obtained DNA isolates are so well purified of heme that there is no need for additional substances that have a protective effect on the DNA polymerase used in the subsequent amplification reaction. An additional advantage is that the blood sample subjected to the process can be purified using numerous commercially available DNA isolation kits, while a specific DNA isolation kit allows obtaining DNA only from bacteria or fungi or leukocytes. The attempts to use kits without initial preparation of blood, via the exemplary methodology described herein, resulted in obtaining DNA with a highly polluted heme and the inability to obtain the nucleic acids from fungal cells.

Samples without pre-treatment according to the exemplary embodiment and after the preparation were further processed using five ready commercially available DNA isolation kits (marked with the following letters A, B, C, D, E). In the most useful kit A, there was obtained the sensitivity of microorganisms indication at the level of $E.\ coli$-$10^1$ CFU/ml; $S.\ aureus$-$3\times10^2$ CFU/ml; $C.\ albicans$-$4\times10^2$ CFU/ml; $Aspergillus$ spp. $1.2\times10^2$ CFU/ml.

The results of the example of five commercial kits for DNA isolation are shown, where:

Exemplary methods are further described in the following examples.

EXAMPLE 1

Isolation of DNA from any species of microorganism from blood:

1. add 1.5 ml of whole blood to 6 ml of 0.17 M ammonium chloride,
2. incubate the samples for 20 minutes at 37° C.,
3. centrifuge for 10 minutes at 10 000 rpm,
4. remove supernatant,
5. suspend the precipitate in 100 μl of solution of lysozyme (2 mg/ml) and lysostaphin (0.2 mg/ml) in PBS buffer,
6. transfer the samples to tubes with glass beads (700-1100 μm) and subject to mechanical disruption for 20 seconds at a speed of 4.0 m/s,
7. incubate the samples for 30 minutes at 37° C.,
8. add 200 μl 75 mM NaOH,
9. incubate the samples for 10 minutes at 95° C.,
10. centrifuge for 10 minutes at 12 000 rpm,
11. remove the supernatant,
12. add 500 μl of buffer consisting of 50 mM Tris HCl, 10 mM EDTA, 28 mM β-mercaptoethanol (pH=7.5), and lyticase (5 μl stock: 4000 U),
13. incubate the samples for 30 minutes at 37° C.,
14. centrifuge for 10 minutes at 12 000 rpm.

The obtained precipitate is subjected to further preparations, using a commercial DNA isolation kit according to the protocol provided by the kit manufacturer's procedure. The procedure results in obtaining the DNA ready for further stages of the analysis, e.g. performing a PCR reaction to detect microorganisms.

EXAMPLE 2

Isolation of bacterial DNA from blood:

1. add 1.5 ml of whole blood to 6 ml of 0.17 M ammonium chloride,
2. incubate the samples for 20 minutes at 37° C.,
3. centrifuge for 10 minutes at 10 000 rpm,
4. remove supernatant,
5. suspend the precipitate in 100 μl of solution of lysozyme (2 mg/ml) and lysostaphin (0.2 mg/ml) in PBS buffer,
6. transfer the samples to the tubes with glass beads (700-1100 μm) and subject to mechanical disruption for 20 seconds at a speed of 4.0 m/s,
7. incubate the samples for 30 minutes at 37° C.,
8. centrifuge for 10 minutes at 12 000 rpm.

The obtained precipitate is subjected to further preparations, using a commercial DNA isolation kit according to the protocol provided by the kit manufacturer's procedure. The procedure results in obtaining the DNA ready for further stages of the analysis, e.g. performing a PCR reaction to detect bacteria.

EXAMPLE 3

Isolation of fungal DNA from blood:
1. add 1.5 ml of whole blood to 6 ml of 0.17 M ammonium chloride,
2. incubate the samples for 20 minutes at 37° C.,
3. centrifuge for 10 minutes at 10 000 rpm,
4. remove supernatant,
5. transfer the samples to tubes with glass beads (700-1100 μm) and subject to mechanical disruption for 20 seconds at a speed of 4.0 m/s,
6. add 200 μl of 50 mM NaOH,
7. incubate the samples for 10 minutes at 95° C.,
8. centrifuge for 10 minutes at 12 000 rpm,
9. remove supernatant,
10. add 500 μl of buffer consisting of 50 mM Tris HCl, 10 mM EDTA, 28 mM β-mercaptoethanol (pH=7.5), and lyticase (5 μl stock: 4000 U),
11. incubate the samples for 30 minutes at 37° C.,
12. centrifuge for 10 minutes at 12 000 rpm.

The obtained precipitate is subjected to further preparations, using a commercial DNA isolation kit according to the protocol provided by the kit manufacturer's procedure. The procedure results in obtaining the DNA ready for further stages of the analysis, e.g. performing a PCR reaction to detect fungi.

Of course these methods are exemplary and alterations thereto are possible by those having skill in the relevant technology.

Thus the example embodiments and arrangements achieve improved capabilities, eliminate difficulties encountered in the use of prior methods and systems, and attain the desirable results described herein.

In the foregoing description, certain terms have been used for brevity, clarity and understanding. However, no unnecessary limitations are to be implied therefrom because such terms are used for descriptive purposes and are intended to be broadly construed. Moreover the descriptions and illustrations herein are by way of examples and the invention is not limited to the features shown and described.

Further, it should be understood that features and/or relationships associated with one embodiment can be combined with features and/or relationships from other embodiments. That is, various features and/or relationships from various embodiments can be combined in further embodiments. The inventive scope of the disclosure is not limited to only the embodiments shown or described herein.

Having described the features, discoveries and principles of the exemplary embodiments, the manner in which they are utilized and carried out, and the advantages and useful results attained, the new and useful arrangements, combinations, methodologies, structures, devices, elements, combinations, operations, processes and relationships are set forth in the appended claims.

We claim:

1. A method for simultaneous isolation of microbial DNA from blood from all types of organisms, irrespective of the structures of the cells, comprising:
   a) adding a whole blood sample to an aqueous solution of ammonium chloride at a concentration of 0.10-0.25 M, in a ratio of 1:3 to 1:6 to the volume of the blood sample, incubating the sample at a temperature of 35° C. to 40° C., for 15 to 30 minutes, subjecting the sample to centrifugation, and removing the supernatant to provide precipitate;
   b) suspending the precipitate obtained in step (a) in a solution of lysozyme at a concentration of 2 mg/ml to 5 mg/ml and lysostaphin at a concentration of 0.2 mg/ml to 0.5 mg/ml in PBS buffer, mixing the suspension, separating the suspension to form a supernatant and a remaining material, and removing the supernatant from the remaining material;
   c) subjecting the remaining material obtained in step (b) to mechanical disintegration;
   d) incubating the remaining material at a temperature of 35° C. to 39° C., from 20 to 50 minutes;
   e) after step (d), adding a hydroxide solution at a concentration of 0.65 mM to 0.8 mM, in a ratio of 1:1 to 1:3 in relation to the volume of remaining material of step (c); incubating at a temperature of 80° C. to 95° C., for 5 to 10 minutes; centrifuging the incubated material, and removing the supernatant to provide a further material; adding to the further material, a buffer having a pH of about 7.5, containing Tris HCL, EDTA, and β-mercaptoethanol, and lyticase with enzymatic activity of 30 U to 50 U; and incubating the buffered suspension at a temperature of 35° C. to 39° C., from 20 to 50 minutes;
   f) subjecting the buffered suspension produced in (d) to centrifugation, and removing the supernatant to provide a new precipitate; and
   g) isolating the DNA from the new precipitate obtained in step (f).

2. A method according to claim 1, wherein in step (c) the mechanical disintegration is carried out with glass beads.

3. A method according to claim 1, wherein step (e) is carried out with buffer that consists essentially of 50 mM Tris HCl, 10 mM EDTA and 28 mM β-mercaptoethanol.

4. The method according to claim 1, where the mixing step in step (b) is selected from the group consisting of vortexing and shaking.

5. The method according to claim 1, where the hydroxide solution in step (e) is selected from the group consisting of NaOH and KOH.

* * * * *